US00PP11182P

United States Patent [19]

Stiekema

[11] Patent Number: Plant 11,182

[45] Date of Patent: Jan. 18, 2000

[54] APPLE TREE NAMED 'STIEKEMA 1'

[76] Inventor: Paul Stiekema, 3961 Barrett Dr., Hood River, Oreg. 97031

[21] Appl. No.: 08/942,861

[22] Filed: Oct. 2, 1997

[51] Int. Cl.[7] ..... A01H 5/00

[52] U.S. Cl. ..... Plt./162

[58] Field of Search ..... Plt./34.1, 161, Plt./162

*Primary Examiner*—Howard J. Locker
*Assistant Examiner*—Melissa L. Kimball
*Attorney, Agent, or Firm*—Klarquist Sparkman Campbell Leigh Whinston, LLP

[57] ABSTRACT

A new and distinct variety of apple tree named is provided that is distinguished by the following combination of characteristics (in comparison to 'Obrogala'): (1) fruit that are significantly larger and have a deeper and wider cavity, larger basin, and longer and thicker stem; (2) intense red fruit coloration that covers approximately 90-100% of the fruit surface; (3) leaves having a bronze appearance that is most evident in young leaves; (4) leaves that are smaller, have fewer and less significant marginal undulations and thus appear flatter, have margins with finer and sharper serrations, and leaf tips that are more pointed and end less abruptly; (5) shorter leaf petioles; (6) slightly less vigor; and (7) thinner branches that tend to terminate sooner, and have a smaller internodal length.

3 Drawing Sheets

BACKGROUND OF THE INVENTION

The present invention comprises a new and distinct variety of apple tree, referred to by the varietal name Stiekema 1.

The parent tree(s) of the new variety originated as a limb mutation found on a tree of the Obrogala cultivar (U.S. Plant Pat. No. 8,621) that was discovered in a cultivated area in Hood River, Oreg. Trees of the new variety have been asexually reproduced by budding in Hood River, Oreg., on M7 and M9 rootstock.

The Stiekema 1 variety was compared to the Obrogala variety. Fruit was harvested from trees grown at Hood River, Oreg. and were from trees of similar age grafted on M7 and M9 rootstock. This invention has not been observed under all possible environmental conditions. However, the following combination of traits have been repeatedly observed in asexually propagated progeny and are determined to be the basic characteristics of this invention, which in combination distinguish this variety of apple as a new and distinct variety: (1) the fruit are significantly larger than fruit from 'Obrogala' and from other standard Gala-type apple varieties, and, compared to 'Obrogala', have a deeper and wider cavity, larger basin, and longer and thicker stem; (2) an intense red fruit coloration that is similar in shade and intensity to 'Obrogala' and that covers approximately 90–100% of the fruit surface; (3) the leaves are different in color than 'Obrogala', having a bronze appearance that is most evident in young leaves: (4 ) leaves that are smaller, have fewer and less significant marginal undulations and thus appear flatter, have margins with finer and sharper serrations, and leaf tips that are more pointed and end less abruptly compared to 'Obrogala'; (5) the leaf petiole is shorter than 'Obrogala'; (6) the tree is slightly less vigorous than 'Obrogala'; (7) and branches are thinner, tend to terminate sooner, and have a smaller internodal length than 'Obrogala'.

Asexual reproduction by budding and grafting in Hood River, Oreg. shows that these characteristics are established and transmitted through succeeding asexual propagations.

BRIEF DESCRIPTION OF THE PHOTOGRAPHS

DETAILED DESCRIPTION

The following is a detailed description of the invention based on plants produced under orchard practices in Hood River, Oreg., during the 1996 and 1997 growing seasons.

Color references are made in accordance with The Royal Horticultural Society (R.H.S.) Colour Chart (1976), and in some cases to Ridgway's Color Standards, except where general color terms of ordinary dictionary significance are obvious or where otherwise indicated.

All trees of the new variety, insofar as I have been able to observe them, have been identical in all the characteristics described below. Except where otherwise noted, the trees of the new variety and the comparison variety were grafted to M7 or M9 rootstock.

Species: *Malus domestica.*
Parentage: Limb mutation of 'Obrogala'.
Propagation: Holds to distinguishing characteristics through succeeding propagation by budding and grafting.
Locality where grown and observed: Hood River, Oreg.
Tree: Medium small; vigorous (slightly less vigorous than 'Obrogala'); spreading; low; round-topped; medium-slow growing.

Figure 3:
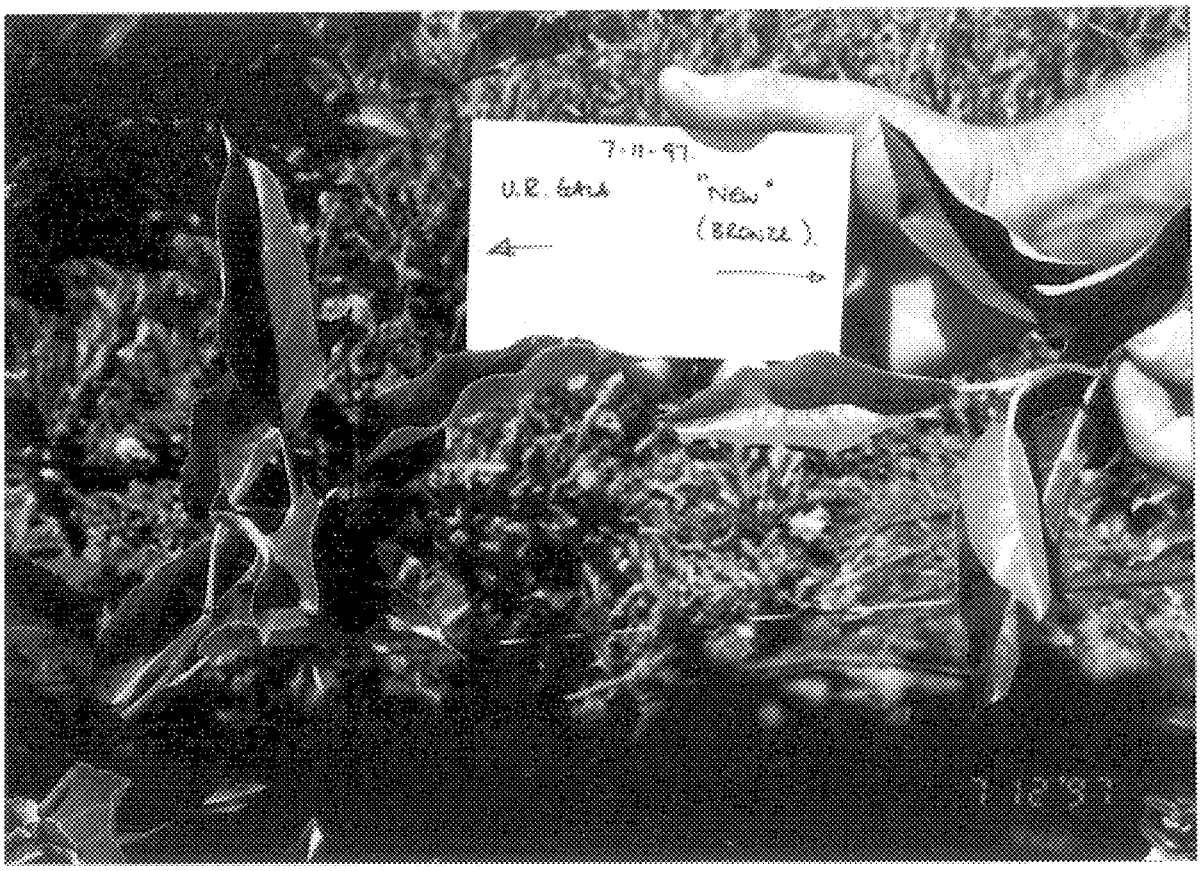
FIG. 3 is a view of leaves of 'Obrogala' (left) and 'Stiekema 1' (right) showing the bronzer coloration of leaves of 'Stiekema 1'.

- *Bark.*—Numerous medium-large white/creamy lenticels that are irregularly rounded.
- *Trunk.*—Medium smooth.
- *Branches.*—Thinner than 'Obrogala' (6.5 mm vs. 7.1 mm); smooth, much branching, tending to terminate sooner than 'Obrogala'; light mouse gray.
- *Internodes* (*average length*). —35 mm (vs. 42 mm for 'Obrogala').
- *Leaves.*—Size: Smaller than 'Obrogala': ave. length 13.14 cm (vs. 13.83 cm for 'Obrogala'; ave. width 7.51 cm (vs. 8.31 cm for 'Obrogala'). Shape: Generally similar to 'Obrogala' but leaf tips are more pointed and end less abruptly. Color: R.H.S. 137B (vs. 139A for 'Obrogala'). Underside of leaf having a color which is like the color of the upper side of the leaf, but lighter. Terminal leaves have a bronzer appearance than 'Obrogala', with young leaves having a pronounced bronze appearance which is variable with the maturity of the leaf (color like R.H.S. 153D being one example) (FIG. 3). Margin: Crenate; finely serrate (41 serrations per 100 mm vs. 35 per 100 mm for 'Obrogala'); serrations are sharper than 'Obrogala'; fewer and less significant marginal undulations than 'Obrogala', giving a flatter appearance. Petiole: Shorter than 'Obrogala' (2.44 mm vs. 3.33 mm).

*Flower.*—Medium size, appears slightly larger than 'Obrogala'; white with pink fading to white on the under side like 'Obrogala'. Fragrance, typical of 'Obrogala', slight. Flowering period similar to 'Obrogala'. Although variable depending upon weather conditions, during the 1997 growing season in Hood River, Oreg., first bloom was observed to occur on about Apr. $10^{th}$ with last bloom observed on Apr. $29^{th}$.

*Reproductive organs.*—Like 'Obrogala' except that flowers and ovules appear slightly larger on average than those of 'Obrogala'.

*Pollinators.*—No specific pollinator required, appears to be compatible with mid-season diploid apple trees. Crab apple trees have been used as pollinators.

Fruit (Description is of fruit of 'Stiekemal 1' and 'Obrogala' varieties grown on M26 rootstock):

*Size.*—Large to very large, fruit harvested in September 1997 averaged about 2.97 to 3.13 inches in diameter about 230 to 280 grams in comparison to 'Obrogala' fruit which was about 165 to 180 grams, much larger than fruit of standard Gala-type varieties.

*Form.*—Generally globose and approaching a conical configuration. Lobal points of immature fruit have distinctive ridges up the sides.

*Cavity.*—Symmetrical and abrupt at base; apex is acuminate. Deeper and broader than 'Obrogala'.

*Basin* (*calyx*).—Larger than 'Obrogala', slightly open (more open than other Gala varieties), lanceolate, and reflexed from base at apex.

*Stem.*—Length about 29 mm (vs. 22 mm for 'Obrogala', thickness 4.5 mm (vs. 3.5 mm for 'Obrogala'.

Figure 1:
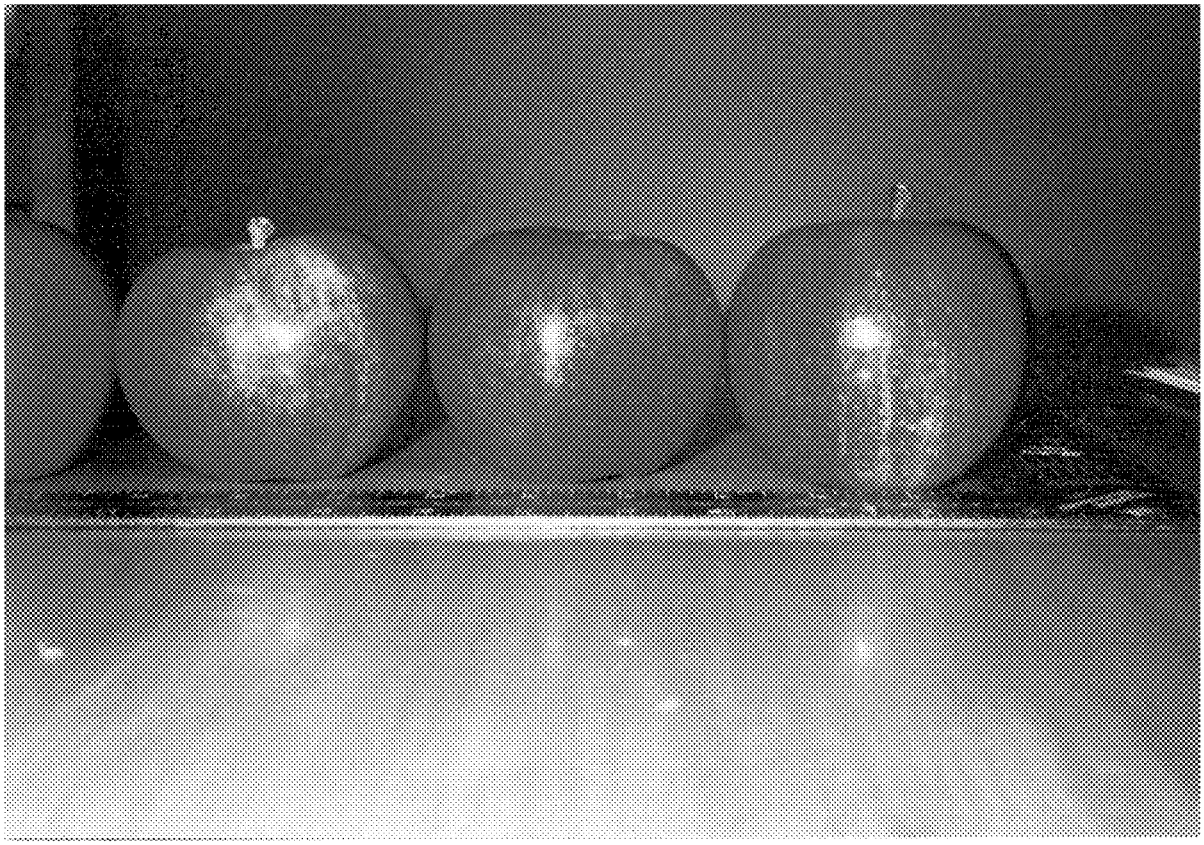
FIG. 1 is a view of mature fruit of the variety.
Figure 2:
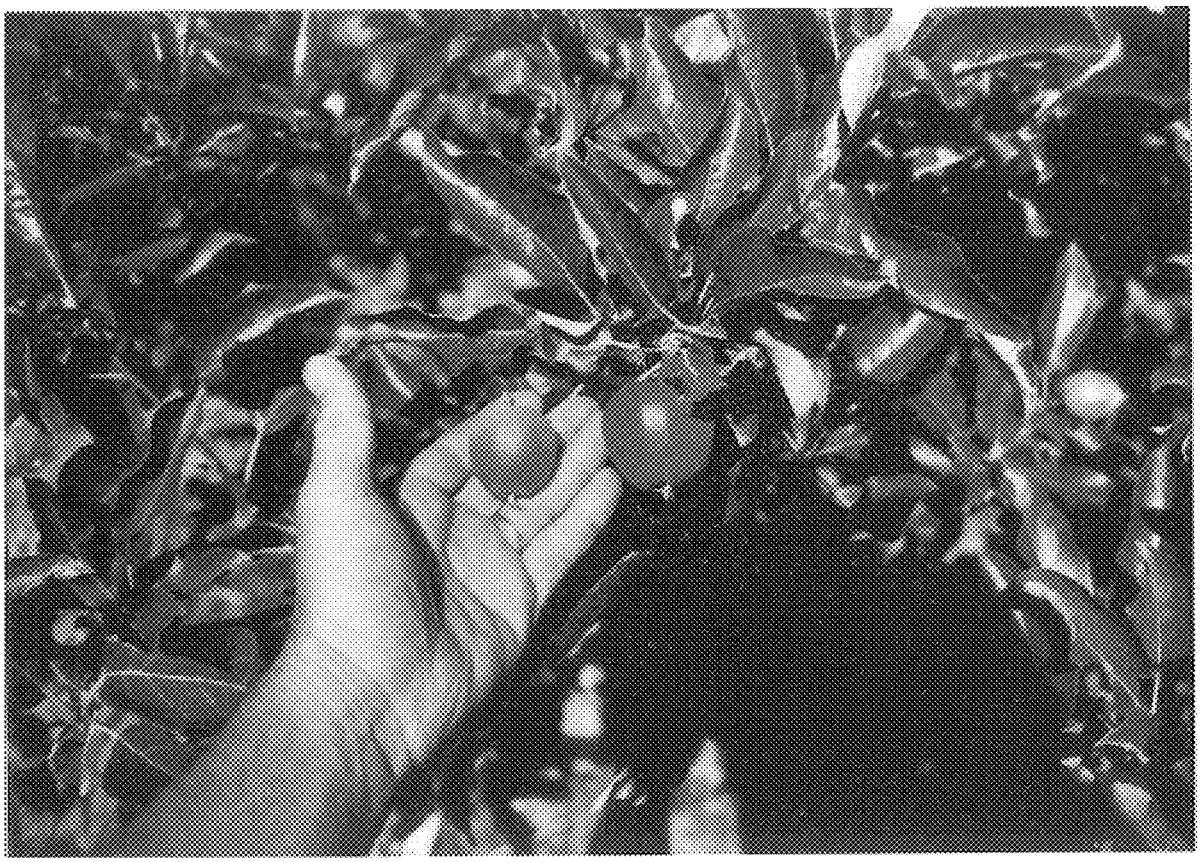
FIG. 2 is a view of immature fruit of 'Obrogala' (left) and 'Stiekema 1' (right) showing development of intense red coloration over 90–100 percent of the fruit surface of 'Stiekema 1' earlier than for 'Obrogala'.

*Skin.*—Thin, smooth, glossy, and waxed. No significant russeting observed, typical of 'Obrogala'. Color of mature fruit and color markings similar to 'Obrogala' (see FIG. 1): ground color, Solid Nopal Red, Plate 1 3 OR (Ridgway's Color Standards) blushed uniformly as a solid color covering approximately 90–100 percent of the fruit surface, even in pubescent fruit, i.e., at an earlier stage than 'Obrogala' (see FIG. 2).

*Flesh.*—Juicy, satiny, and crreamy white in appearance. Texture: Firm, tender, fine, and crisp. Maintains crispness after four weeks in common storage flavor: mild, delicate, and rich.

*Quality.*—Best.

*Core.*—Sessile; medium. Bundle area small and oblate in longitudinal section and bundles are inconspicuous, in one whorl. Core lines are clasping, indistinct.

*Seeds.*—Length about 5/16 inch, breadth about 3/16 inch; color, burnt umber Plate XXVIII, Color No. 9", tone m (Ridgway's Color Standards).

*Bearing Habit.*—Annual.

*Maturation.*—Observed to be like 'Obrogala' in Hood River, Oreg., varies with temperature of growing season and desired sugar content of apples. Early to mid-September would be a typical maturation date in Hood River, Oreg. In 1997, fruit picking occurred on Sep. 11, 1997 and last picking took place on Sep. 29, 1997.

*Use.*—Market, dessert.

*Keeping quality.*—Good. PS

I claim:

1. A new and distinct variety of apple tree substantially as herein shown and described.

* * * * *